(12) United States Patent
Kawaguchi et al.

(10) Patent No.: US 8,766,021 B2
(45) Date of Patent: Jul. 1, 2014

(54) PROCESS FOR PRODUCING 2,3,3,3-TETRAFLUOROPROPENE

(75) Inventors: Satoshi Kawaguchi, Tokyo (JP); Hidekazu Okamoto, Tokyo (JP); Yu Takeuchi, Tokyo (JP); Hirokazu Takagi, Tokyo (JP); Kunio Watanabe, Tokyo (JP); Koichi Yanase, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/167,509

(22) Filed: Jun. 23, 2011

(65) Prior Publication Data

US 2011/0319680 A1 Dec. 29, 2011

Related U.S. Application Data

(60) Provisional application No. 61/365,932, filed on Jul. 20, 2010.

(30) Foreign Application Priority Data

Jun. 23, 2010 (JP) ................................. 2010-142666

(51) Int. Cl.
    *C07C 19/08* (2006.01)
(52) U.S. Cl.
    USPC ....................................................... 570/176
(58) Field of Classification Search
    None
    See application file for complete search history.

(56) References Cited

FOREIGN PATENT DOCUMENTS

| | | |
|---|---|---|
| EP | 396974 A1 * | 11/1990 |
| JP | 2-286635 | 11/1990 |
| JP | 2010-510221 | 4/2010 |
| WO | WO 2008/060614 A2 | 5/2008 |
| WO | WO 2009/035130 A2 | 3/2009 |

OTHER PUBLICATIONS

Search Report issued Sep. 20, 2011 in PCT/JP2011/064424 (with English Translation of Category of Cited Documents).
Chemical Dictionary, first edition first printing, Kyoritsu Publishing Co., 1960, p. 437.
Selection of Industrial Reactor Design Examples, First Edition, Baifukan Co., 1984, p. 21.
U.S. Appl. No. 13/167,464, filed Jun. 23, 2011, Takagi, et al.
U.S. Appl. No. 13/167,455, filed Jun. 23, 2011, Okamoto.
U.S. Appl. No. 13/167,285, filed Jun. 23, 2011, Seki, et al.
U.S. Appl. No. 13/167,235, filed Jun. 23, 2011, Kawaguchi, et al.
U.S. Appl. No. 13/167,145, filed Jun. 23, 2011, Takagi, et al.
U.S. Appl. No. 13/167,254, filed Jun. 23, 2011, Kawaguchi, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

In the production of 2,3,3,3-tetrafluoropropene (HFO-1234yf), formation of HFC-254eb as an excessively reduced product is suppressed.
A process for producing 2,3,3,3-tetrafluoropropene, which comprises reacting a raw material compound gas composed of at least one of 1,1-dichloro-2,3,3,3-tetrafluoropropene and 1-chloro-2,3,3,3-tetrafluoropropene, and hydrogen gas, in the presence of a catalyst, wherein the catalyst is a catalyst having palladium supported on active carbon, and the ratio of the number of moles of the hydrogen gas to the number of moles of chlorine atoms in the raw material compound gas ($H_2$/Cl) is at most 0.7.

19 Claims, 1 Drawing Sheet

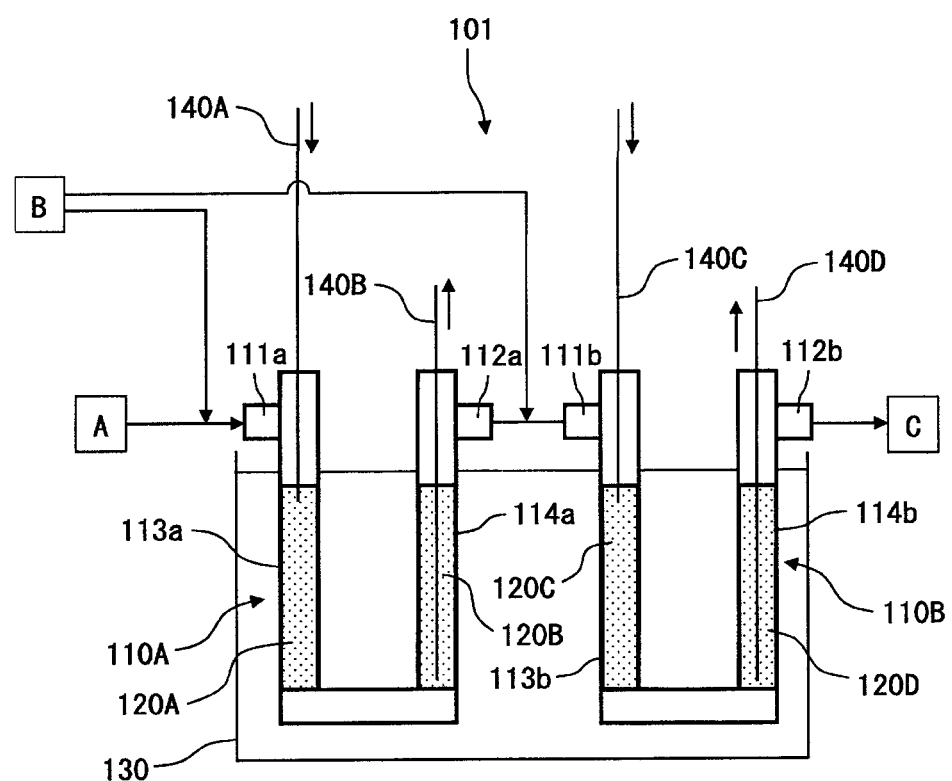

PROCESS FOR PRODUCING 2,3,3,3-TETRAFLUOROPROPENE

TECHNICAL FIELD

The present invention relates to a process for producing 2,3,3,3-tetrafluoropropene.

BACKGROUND ART 2,3,3,3-tetrafluoropropene ($CF_3CF=CH_2$, HFO-1234yf) contains no chlorine and thus is useful as an alternative compound for chlorofluorocarbons to be used for e.g. refrigerants.

As a process for producing HFO-1234yf, a process may, for example, be mentioned wherein 1,1-dichloro-2,2,3,3,3-pentafluoropropane ($CF_3CF_2CHCl_2$, HCFC-225ca) is subjected to a dehydrofluorination reaction to obtain 1,1-dichloro-2,3,3,3-tetrafluoropropene ($CF_3CF=CCl_2$, CFO-1214ya), and then, CFO-1214ya is reacted with hydrogen and reduced to obtain HFO-1234yf.

As a method of reducing CFO-1214ya to obtain HFO-1234yf, the following method (i) may, for example, be mentioned.

(i) A method for obtaining HFO-1234yf by reacting a raw material compound gas composed of CFO-1214ya and a hydrogen gas in the presence of a catalyst having palladium supported on alumina so that the ratio of the number of moles of the hydrogen gas to the number of moles of chlorine atoms in the raw material compound gas ($H_2$/Cl) will be from 0.5 to 2 (Patent Document 1).

However, the method (i) has a problem such that together with HFO-1234yf, an excessively reduced product 1,1,1,2-tetrafluoropropane ($CF_3CHFCH_3$, HFC-254eb) will be formed as a by-product in a large amount.

PRIOR ART DOCUMENT

Patent Document
Patent Document 1: WO2008/060614

DISCLOSURE OF INVENTION

Technical Problem

It is an object of the present invention to provide a process for producing 2,3,3,3-tetrafluoropropene (HFO-1234yf), whereby it is possible to suppress formation of an excessively reduced product HFC-254eb as a by-product.

Solution to Problem

In order to solve the above problem, the present invention has adopted the following construction.

[1] A process for producing 2,3,3,3-tetrafluoropropene, which comprises reacting a raw material compound gas composed of at least one of 1,1-dichloro-2,3,3,3-tetrafluoropropene and 1-chloro-2,3,3,3-tetrafluoropropene, and hydrogen gas, in the presence of a catalyst, wherein the catalyst is a catalyst having palladium supported on active carbon, and the ratio of the number of moles of the hydrogen gas to the number of moles of chlorine atoms in the raw material compound gas ($H_2$/Cl) is at most 0.7.

[2] The process for producing 2,3,3,3-tetrafluoropropene according to the above [1], wherein the supported amount of palladium in the catalyst is from 0.1 to 10 mass % based on the active carbon.

ADVANTAGEOUS EFFECT OF INVENTION

According to the process of the present invention, it is possible to suppress formation of an excessively reduced product HFC-254eb as a by-product.

BRIEF DESCRIPTION OF DRAWING

FIG. 1 is a schematic view illustrating a reaction apparatus used in Examples.

DESCRIPTION OF EMBODIMENT

In the process for producing 2,3,3,3-tetrafluoropropene (HFO-1234yf) of the present invention, a raw material compound gas composed of at least one of 1,1-dichloro-2,3,3,3-tetrafluoropropene ($CF_3CF=CCl_2$, CFO-1214ya) and 1-chloro-2,3,3,3-tetrafluoropropene ($CF_3CF=CHCl$, HCFO-1224yd), and hydrogen gas, are reacted in the presence of a catalyst. That is, the process of the present invention is a process to obtain HFO-1234yf by subjecting the raw material compound and hydrogen to a gas phase reaction in the presence of a catalyst.

CFO-1214ya and HCFO-1224yd will form HFO-1234yf by the reactions represented by the following formulae (1) and (2), respectively.

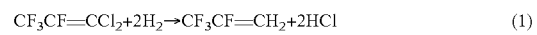

$$CF_3CF=CCl_2 + 2H_2 \rightarrow CF_3CF=CH_2 + 2HCl \quad (1)$$

$$CF_3CF=CHCl + H_2 \rightarrow CF_3CF=CH_2 + HCl \quad (2)$$

For the reaction of the raw material compound gas and the hydrogen gas, specifically, a method may, for example, be mentioned wherein a catalyst layer packed with a catalyst is formed, and to such a catalyst layer, the raw material compound gas and the hydrogen gas are introduced and reacted.

As the catalyst in the process of the present invention, a catalyst having palladium supported on active carbon is used.

The active carbon may be one prepared by using, as a raw material, wood, charcoal, fruit shell, coconut shell, peat, lignite, coal or the like, and one obtained from a plant raw material rather than from a mineral raw material is preferred. Particularly preferred is coconut shell active carbon.

As the shape of the carrier, formed coal having a length of from about 2 to 5 mm, pulverized coal of from about 4 to 50 mesh or granular coal may, for example, be mentioned. Among them, pulverized coal of from 4 to 20 mesh or formed coal is preferred.

The supported amount of palladium in the catalyst is, based on active carbon, preferably from 0.1 to 10 mass %, more preferably from 0.5 to 1 mass %. When the supported amount of palladium is at least the lower limit value, the conversion of the raw material compound gas and the hydrogen gas will be improved. When the above supported amount of palladium is at most the upper limit value, an excessive temperature rise of the catalyst layer by a heat of reaction can easily be controlled, and formation of by-products can easily be reduced.

Further, the catalyst having palladium supported on active carbon may further have a metal other than palladium supported.

The metal other than palladium may, for example, be a Group 8 element such as iron, ruthenium or osmium; a Group 9 element such as cobalt, rhodium or iridium; a Group 10 element such as nickel or platinum; or gold. Such metals other than palladium may be used alone, or two or more of them may be used in combination.

The proportion of the metal other than palladium is preferably from 0.01 to 50 parts by mass, per 100 parts by mass of palladium. The composite catalyst having the metal other than palladium supported together with palladium tends to have higher catalyst durability than the catalyst having only palladium supported alone.

The packed density of the catalyst in the catalyst layer is preferably from 0.5 to 1 g/cm$^3$, more preferably from 0.6 to 0.8 g/cm$^3$. When the packed density of the catalyst is at least the lower limit value, the packed amount of the catalyst per unit volume is large, whereby the amount of gas to be reacted can be increased, and the productivity will be improved. When the packed density of the catalyst is at most the upper limit value, the temperature rise of the catalyst layer due to a heat of reaction can easily be controlled, and it becomes easy to suppress the formation of by-products.

The catalyst layer may be one or more than one. In a case where the catalyst layer is more than one, such a plurality of catalyst layers may be arranged in parallel or in series.

With respect to the ratio of the hydrogen gas to the raw material compound gas to be introduced to the catalyst layer, with a view to suppressing formation of the excessively reduced product HFC-254eb as a by-product, the ratio of the number of moles of the hydrogen gas to the number of moles of chlorine atoms in the raw material compound gas ($H_2$/Cl) is adjusted to be at most 0.7. Such a ratio ($H_2$/Cl) should better be smaller, whereby formation of HFC-254eb can easily be suppressed, and it is preferably at most 0.6, more preferably at most 0.5. Further, the ratio ($H_2$/Cl) is preferably at least 0.1, more preferably at least 0.2, from the viewpoint of the yield of HFO-1234yr.

The temperature of the catalyst layer during the reaction is preferably at least 50° C., more preferably at least 60° C., since the boiling point of CFO-1214ya is 46° C., and the boiling of HCFO-1224yd is assumed to be from 4 to 10° C., and from the viewpoint of the reactivity.

Further, in the process of the present invention, the maximum temperature of the catalyst layer is maintained to be preferably at most 130° C., more preferably at most 100° C. during the reaction with a view to suppressing formation of a by-product. That is, in the process of the present invention, when the raw material compound gas and the hydrogen gas introduced into the catalyst layer are reacted, a heat of reaction is generated, and therefore, it is preferred to suppress an excessive temperature rise of the catalyst layer due to the heat of reaction and to adjust the maximum temperature of the catalyst to be at most the above upper limit value.

As a method for measuring the maximum temperature of the catalyst layer, the following measuring method employing an insertion-type thermometer may, for example, be mentioned.

In the reaction of the raw material compound gas and the hydrogen gas in the catalyst layer, firstly, the catalyst at the gas inlet portion contributes to the reaction, and as the catalyst at the gas inlet portion deteriorates, the catalyst inside thereof will contribute to the reaction, and in such a manner, the reaction point in the catalyst layer gradually moves towards to the gas outlet side. That is, the portion showing the maximum temperature of the catalyst layer moves along with the movement of the reaction point of the raw material compound gas and the hydrogen gas. Accordingly, by preliminarily positioning the measuring portion of the insertion-type thermometer at the gas inlet portion of the catalyst layer and moving the measuring portion along with the progress of the reaction, the maximum temperature of the catalyst layer can be measured.

As a method to maintain the maximum temperature of the catalyst layer to be at most the above upper limit value, a method (method ($\alpha$)) of introducing the hydrogen gas dividedly to the catalyst layer is preferred from such a viewpoint that the productivity can easily be maintained to be high while controlling the maximum temperature of the catalyst layer to be low. If the hydrogen gas is introduced dividedly to plural portions of the catalyst layer, it is possible to disperse the reaction points of the raw material compound gas and the hydrogen gas in the catalyst layer without changing the amount of the raw material compound gas to be introduced, whereby generation of the heat of reaction is not localized at one portion. Therefore, it is possible to easily suppress local excessive heat generation in the catalyst layer, without lowering the productivity.

Introduction of the hydrogen gas in the method ($\alpha$) may be divided into two portions or divided into three or more portions. It is preferred to divide the introduction into two portions, whereby the process can be simplified.

The divided proportions of the hydrogen gas to be introduced dividedly to at least two portions in the catalyst layer are preferably such that the respective gas amounts divided are equal amounts, whereby it is easy to maintain the maximum temperature of the catalyst layer to be low.

Further, with respect to the positions for introducing the hydrogen gas in the case of introducing the hydrogen gas dividedly, a part of the divided hydrogen gas may be introduced together with the raw material compound gas to the catalyst layer, and the rest of hydrogen gas may be introduced to any positions at intermediate portions of the catalyst layer depending upon the number of divisions and the divided proportions.

In a case where there are two or more catalyst layers, if they are arranged in parallel, the raw material compound gas and the hydrogen gas are, respectively dividedly, introduced to such catalyst layers. If the two or more catalyst layers are arranged in series, the divided introduction of the hydrogen gas may, for example, be carried out by a method wherein a part of the hydrogen gas is introduced together with the raw material compound gas to the first stage catalyst layer, and the rest is introduced to the catalyst layers of the second or subsequent stages.

Further, as a method for controlling the maximum temperature of the catalyst layer other than the method ($\alpha$), a method (method ($\beta$)) of letting an inert gas flow in the catalyst layer together with the raw material compound gas and the hydrogen gas, may be mentioned. By adjusting the concentration of the raw material compound gas and the hydrogen gas flowing in the catalyst layer by letting the inert gas flow, it is possible to suppress an excessive temperature rise of the catalyst layer by a heat of reaction.

As such an inert gas, nitrogen gas, etc. may, for example, be mentioned.

The amount of the inert gas to be introduced to the catalyst layer is preferably at least 0.1 mol, more preferably at least 0.5 mol, per 1 mol of the raw material compound gas, from such a viewpoint that it is thereby easy to maintain the maximum temperature of the catalyst layer to be low, to reduce formation of by-products and to suppress deterioration of the catalyst. Further, the amount of the inert gas to be introduced is preferably at most 10 mol, more preferably at most 4 mol, per 1 mol of the raw material compound gas, from the viewpoint of the recovery rate of the inert gas.

For controlling the maximum temperature of the catalyst layer, it is preferred to use the method ($\alpha$) alone or to use the methods ($\alpha$) and ($\beta$) in combination. Otherwise, the maximum temperature of the catalyst layer may be controlled only by the method ($\beta$).

The reaction pressure is preferably atmospheric pressure from the viewpoint of the operation efficiency.

The contact time of the raw material compound gas to the catalyst is preferably from 4 to 60 seconds, more preferably from 8 to 40 seconds. In a case where two or more catalyst layers are arranged in parallel, the contact time of the raw material compound gas to the catalyst preferably satisfies the above range in each of the catalyst layers. In a case where two or more catalyst layers are arranged in series, the contact time of the raw material compound gas to the catalyst is preferably such that the total of the contact times of all catalyst layers to the catalyst satisfies the above range.

In the process of the present invention, the linear velocity u of the raw material compound gas represented by the following formula (I) in the catalyst layer, varies depending upon the diameter of the reaction tube, but in the case of the diameter of the reaction tube which is commonly used for a gas phase reduction reaction, it is preferably from 0.1 to 100 cm/sec., more preferably from 1 to 30 cm/sec. When the linear velocity u of the raw material compound gas is at least the lower limit value, the productivity will be improved. Especially when the gas linear velocity is at least 1 cm/sec., the gas is likely to flow uniformly in the catalyst layer. When the linear velocity u of the raw material compound gas is at most the upper limit, the conversion of the raw material compound gas and the hydrogen gas will be improved. Especially when the gas linear velocity is at most 30 cm/sec., the temperature control in the vicinity of the reaction point due to heat generation will be easy.

$$u = W \times V/S \tag{I}$$

In the formula (I), W is the concentration (mol %) of the raw material compound gas in the entire gas flowing through the catalyst layer, V is the flow rate ($cm^3$/sec) of the entire gas flowing through the catalyst layer, and S is the cross-sectional area ($cm^2$) of the catalyst layer to the flow direction of the gas.

As a reactor to be used for the process of the present invention, a known reactor capable of forming a catalyst layer having a catalyst packed, may be mentioned.

As the material for the reactor, glass, iron, nickel or an alloy containing such a metal as the main component may, for example, be mentioned.

The formed gas after the reaction contains, in addition to the desired product HFO-1234yf, an unreacted raw material, HCFO-1224yd formed as a reaction intermediate and HCl.

HCl contained in the formed gas can be removed by blowing the formed gas into an alkali aqueous solution for its neutralization. The alkali to be used for such an alkali aqueous solution may, for example, be sodium hydroxide or potassium hydroxide.

As a method for recovering HFO-1234yf from the formed gas, a known method such as distillation may, for example, be employed.

The raw material compound gas is a gas composed of at least one of CFO-12114ya and HCFO-1224yd.

CFO-1214ya can be produced by a known method. For example, a method may be mentioned wherein 1,1-dichloro-2,2,3,3,3-pentafluoropropane ($CHCl_2CF_2CF_3$, HCFC-225ca) is subjected to a dehydrofluorination reaction by contacting it with an alkali aqueous solution in the presence of a phase-transfer catalyst. For such a reaction, a mixture of isomers of dichloropentafluoropropane (HCFC-225) including HCFC-225ca may be used, and only HCFC-225ca in the mixture of isomers may selectively be dehydrofluorinated by the above phase-transfer catalyst. After the reaction, CFO-1214ya can be separated and recovered by a known method such as distillation.

The above mixture of isomers can be produced by reacting tetrafluoroethylene and dichlorofluoromethane in the presence of a catalyst such as aluminium chloride. The mixture of isomers obtainable by such a reaction contains HCFC-225ca and 1,3-dichloro-1,2,2,3,3-pentafluoropropane ($CHClFCF_2CClF_2$, HCFC-225cb) as the main components, and further contains a small amount of 2,2-dichloro-1,1,3,3,3-pentafluoropropane ($CHF_2CCl_2CF_3$, HCFC-225aa), 2,3-dichloro-1,1,2,3,3-pentafluoropropane ($CHF_2CClFCClF_2$, HCFC-225bb), etc.

As such a mixture of isomers, a commercial product may be employed. As such a commercial product, ASAHIKLIN AK225 (tradename, manufactured by Asahi Glass Company, Limited, mixture of 48 mol % of HCFC-225ca and 52 mol % of HCFC-225cb) may, for example, be mentioned.

As the above phase-transfer catalyst, tetrabutylammonium bromide (TBAB) is preferred.

HCFO-1224yd is formed as an intermediate at the time of obtaining HFO-1234yf by reacting CFO-1214ya with hydrogen.

HCFO-1224yd recovered from the formed gas after the reaction may be reacted, as the raw material compound gas together with CFO-1214ya, with the hydrogen gas, or separately from CFO-1214ya, HCFO-1224yd may alone be reacted with the hydrogen gas.

According to the process of the present invention as described in the foregoing, the raw material compound gas and the hydrogen gas are reacted by means of a catalyst having palladium supported on active carbon, as the catalyst, so that the ratio of the number of moles of the hydrogen gas to the number of moles of chlorine atoms in the raw material compound gas ($H_2$/Cl) will be at most 0.7, whereby formation of the excessively reduced product HFC-254eb as a by-product can be suppressed. Consequently, the amounts of the desired product HFO-1234yf and HCFO-1224yd convertible to HFO-1234yf will increase, whereby it is possible to efficiently produce highly pure HFO-1234yf.

EXAMPLES

Now, the present invention will be described in further detail with reference to Examples and Comparative Examples. However, it should be understood that the present invention is by no means restricted by the following description. Examples 1 to 3 are working Examples of the present invention and Examples 4 and 5 are Comparative Examples.

Example 1

For the production of HFO-1234yf ($CF_3CF=CH_2$), a reaction apparatus 101 shown in FIG. 1 was used.

As shown in FIG. 1, the reaction apparatus 101 is provided with two reaction tubes 110A and 110B and a salt bath 130 for immersion of such reaction tubes 110A and 110B. The reaction tube 110A has catalyst-packing portions 113a and 114a at two positions on the inlet 111a side and the outlet 112a side. Likewise, the reaction tube 110B has catalyst-packing portions 113b and 114b at two positions on the inlet 111b side and the outlet 112b side. The outlet 112a of the reaction tube 110A is connected by piping to the inlet 111b of the reaction tube 110B.

As the reaction tubes 110A and 110B, reaction tubes made of Inconel (registered trademark) 600 and having an inner diameter of 2.54 cm and a length of 100 cm, were used. Further, as a catalyst, a catalyst having 0.5 mass % of palladium supported on coconut shell active carbon, was used, and such a catalyst was packed in the catalyst-packing portions 113a and 114a of the reaction tube 110A to form a catalyst layer 120A and a catalyst layer 120B each having a height of 40 cm. Likewise, the above catalyst was packed in the respective catalyst-packing portions 113b and 114b of the reaction tube 110B to form a catalyst layer 120C and a catalyst layer 120D each having a height of 40 cm. The packed density of the catalyst in catalyst layers 120A to 120D was adjusted to be 0.73 g/cm³.

Then, the reaction tube 110A and the reaction tube 110B were immersed in the salt bath 130 so that all of the catalyst layers 120A to 120D were immersed, and the catalyst layers 120A to 120D were heated to 80° C.

Then, a raw material compound gas (A) having CFO-1214ya ($CF_3CF=CCl_2$) and HCFO-1224yd ($CF_3CF=CHCl$) mixed in a ratio of 6:1, and hydrogen gas (B) were permitted to flow through reaction tubes 110A and 110B to obtain formed gas (C).

The contact time of the raw material compound gas (A) to the catalyst layers 120A to 120D was adjusted to be 23 seconds, and the ratio of the number of moles of the hydrogen gas to the number of moles of chlorine atoms in the raw material compound gas (A) ($H_2/Cl$) was adjusted to be 0.43. The linear velocity u of the raw material compound gas (A) was adjusted to be 7 cm/sec.

Further, with respect to the hydrogen gas (B), 50% of the total introduced amount was introduced from the inlet 111a of the reaction tube 110A together with the raw material compound gas (A), and the rest of 50% was introduced to the piping portion connecting the reaction tube 110A and the reaction tube 110B. That is, in the catalyst layer having a length of 160 cm and consisting of catalyst layers 120A to 120D, the hydrogen gas (B) was dividedly introduced at two portions i.e. the catalyst layer 120A (0 cm point) and the catalyst layer 120C (80 cm point).

Further, the maximum temperature of the catalyst layers 120A to 120D during the reaction was measured by insertion-type thermometers 140A to 140D inserted respectively to such catalyst layers and found to be at most 100° C.

Example 2 and 3

Formed gas (C) was obtained in the same manner as in Example 1 except that the ratio ($H_2/Cl$) was changed as shown in Table 1.

Example 4

Formed gas (C) was obtained in the same manner as in Example 1 except that the catalyst was changed to a catalyst having 0.5 mass % of palladium supported on alumina, and the ratio ($H_2/Cl$) was changed as shown in Table 1.

Example 5

Formed gas (C) was obtained in the same manner as in Example 1 except that the ratio ($H_2/Cl$) was changed as shown in Table 1.

[Evaluation Method]

The formed gas (C) thus obtained was analyzed by gas chromatography (GC), and the conversion ratio X (unit: %) to HFO-1234yf, the conversion ratio Y (unit: %) to HCFO-1224yd, and the conversion ratio Z (unit: %) to HFC-254eb ($CF_3CHFCH_3$) were calculated by the following formulae (II) to (IV), respectively.

$$X=[c/((a+b)/2)] \times 100 \quad (II)$$

$$Y=[d/((a+b)/2)] \times 100 \quad (III)$$

$$Z=[e/((a+b)/2)] \times 100 \quad (IV)$$

(In the above formulae, a represents the number of moles of CFO-1214ya in the raw material compound gas (A), b the number of moles of HCFO-1224yd in the raw material compound gas (A), c the number of moles of HFO-1234yf in the formed gas (C), d the number of moles of HCFO-1224yd in the formed gas (C) and e the number of moles of HFC-254eb in the formed gas (C).)

The evaluation results in each Example are shown in Table 1, and the area ratio (unit: %) in the GC analysis of the formed gas (C) is shown in Table 2. Here, in Table 1, "Pd/C" represents the catalyst having palladium supported on coconut shell active carbon, and "$Pd/Al_2O_3$" means a catalyst having palladium supported on alumina. Further, in Table 2, compounds having Freon Nos. 1243zf and 263fb are by-products being excessively reduced products, and compounds having Freon Nos. 244eb and 234ea are compounds which can be recycled as reaction intermediates.

TABLE 1

|  | Ex. 1 | Ex. 2 | Ex. 3 | Ex. 4 | Ex. 5 |
|---|---|---|---|---|---|
| Catalyst | Pd/C | Pd/C | Pd/C | Pd/Al₂O₃ | Pd/C |
| Ratio (H₂/Cl) | 0.43 | 0.54 | 0.625 | 0.5 | 0.75 |
| Conversion ratio X to HFO-1234yf [%] | 56.4 | 61.1 | 56.2 | 48.8 | 66.6 |
| Conversion ratio Y to HCFO-1224yd [%] | 35.5 | 23.8 | 18.5 | 23.3 | 13.1 |
| Conversion ratio Z to HFC-254eb [%] | 6.3 | 11.4 | 15.7 | 25.4 | 18.3 |
| X + Y [%] | 91.9 | 84.9 | 74.7 | 72.2 | 79.7 |

TABLE 2

Unit: %

| Compound | Number | Ex. 1 | Ex. 2 | Ex. 3 | Ex. 4 | Ex. 5 |
|---|---|---|---|---|---|---|
| CF₃CF=CH₂ | 1234yf | 26.70 | 34.21 | 39.30 | 25.29 | 47.66 |
| CF₃CF=CCl₂ | 1214ya | 51.65 | 43.96 | 41.46 | 49.38 | 31.20 |
| CF₃CF=CHCl | 1224yd | 16.78 | 13.30 | 9.82 | 10.99 | 8.17 |
| CF₃CHFCH₂Cl | 244eb | 1.49 | 2.00 | 1.00 | 1.46 | 1.45 |
| CF₃CHFCCl₂ | 234ea | 0.00 | 0.00 | 0.01 | 0.00 | 0.00 |
| CF₃CH=CH₂ | 1243zf | 0.00 | 0.00 | 0.00 | 0.00 | 0.00 |
| CF₃CH₂CH₃ | 263fb | 0.18 | 0.00 | 0.18 | 0.16 | 0.21 |
| CF₃CHFCH₃ | 254eb | 2.97 | 6.37 | 8.17 | 11.97 | 11.21 |

As shown in Tables 1 and 2, in Examples 1 to 3 wherein a catalyst having palladium supported on active carbon was used, and the ratio ($H_2/Cl$) was adjusted to be at most 0.7, formation of the excessively reduced product HFC-254eb as a by-product was lowered as compared with Example 4 wherein a catalyst having palladium supported on alumina was used and Example 5 wherein the ratio ($H_2/Cl$) exceeded 0.7. Further, in Examples 1 to 3, the total value of the conversion ratios X and Y was high, and the conversion ratios to the desired product HFO-1234yf and to HCFO-1224yd which can be recycled, were high.

Further, when Examples 1 to 3 were compared, the smaller the ratio ($H_2/Cl$), the higher the effect to suppress formation of by-product HFC-254eb.

INDUSTRIAL APPLICABILITY

HFO-1234yf obtained by the process of the present invention has high purity, as formation of excessively reduced product HFC-254eb as a by-product is suppressed. Therefore, it is useful as e.g. a refrigerant to replace chlorofluorocarbons.

REFERENCE SYMBOLS

101: Reaction apparatus
120A to 120D: catalyst layers
A: raw material gas
B: hydrogen gas
C: nitrogen gas

What is claimed is:

1. A process for producing 2,3,3,3-tetrafluoropropene, which comprises reacting a raw material compound gas composed of at least one of 1,1-dichloro-2,3,3,3-tetrafluoropropene and 1-chloro-2,3,3,3-tetrafluoropropene, and hydrogen gas, in the presence of a catalyst, wherein the catalyst is a catalyst having palladium supported on active carbon, and the ratio of the number of moles of the hydrogen gas to the number of moles of chlorine atoms in the raw material compound gas ($H_2/Cl$) is at most 0.6.

2. The process for producing 2,3,3,3-tetrafluoropropene according to claim 1, wherein the supported amount of palladium in the catalyst is from 0.1 to 10 mass % based on the active carbon.

3. The process for producing 2,3,3,3-tetrafluoropropene according to claim 1 or 2, wherein the active carbon is coconut shell active carbon.

4. The process for producing 2,3,3,3-tetrafluoropropene according to claim 1 or 2, wherein the ratio of the number of moles of the hydrogen to the number of moles of chlorine atoms in the raw material compound ($H_2/Cl$) is from 0.1 to 0.6.

5. The process for producing 2,3,3,3-tetrafluoropropene according to claim 1 or 2, wherein the raw material compound is 1,1-dichloro-2,3,3,3-tetrafluoropropene, or a mixture of 1,1-dichloro-2,3,3,3-tetrafluoropropene and 1-chloro-2,3,3,3-tetrafluoropropene wherein the proportion of 1,1-dichloro-2,3,3,3-tetrafluoropropene to the total number of moles of both is at least 50 mol %.

6. The process for producing 2,3,3,3-tetrafluoropropene according to claim 1 or 2, wherein the 1-chloro-2,3,3,3-tetrafluoropropene is a compound formed as a byproduct in the production of 2,3,3,3-tetrafluoropropene by a reaction of 1,1-dichloro-2,3,3,3-tetrafluoropropene with hydrogen.

7. The process for producing 2,3,3,3-tetrafluoropropene according to claim 1 or 2, wherein the raw material compound and hydrogen are introduced to a gas inlet portion of the catalyst layer, and hydrogen is introduced from at least one position between the gas inlet portion and a gas outlet portion of the catalyst layer, and wherein the ratio of the total amount of hydrogen including the hydrogen to be introduced to the gas inlet portion of the catalyst layer to the raw material compound is the above-mentioned ratio in the number of moles.

8. The process for producing 2,3,3,3-tetrafluoropropene according to claim 1, wherein the ratio of the number of moles of the hydrogen gas to the number of moles of chlorine atoms in the raw material compound gas ($H_2/Cl$) is at most 0.5.

9. The process for producing 2,3,3,3-tetrafluoropropene according to claim 1, wherein the ratio of the number of moles of the hydrogen gas to the number of moles of chlorine atoms in the raw material compound gas ($H_2/Cl$) is 0.2 to 0.6.

10. The process for producing 2,3,3,3-tetrafluoropropene according to claim 1, wherein the maximum temperature of the catalyst layer is 130° C.

11. The process for producing 2,3,3,3-tetrafluoropropene according to claim 1, wherein a conversion ratio to 2,3,3,3-tetrafluoropropene is 56.2 to 61.1%.

12. The process for producing 2,3,3,3-tetrafluoropropene according to claim 11, wherein a conversion ratio to HFC-254eb is 6.3 to 11.4%.

13. The process for producing 2,3,3,3-tetrafluoropropene according to claim 1, wherein a conversion ratio to HFC-254eb is 6.3 to 11.4%.

14. A process for producing 2,3,3,3-tetrafluoropropene, which comprises introducing a raw material compound composed of 1,1-dichloro-2,3,3,3-tetrafluoropropene, or 1,1-dichloro-2,3,3,3-tetrafluoropropene and 1-chloro-2,3,3,3-tetrafluoropropene, and hydrogen in such an amount that the ratio of the number of moles of hydrogen to the number of moles of chlorine atoms in the raw material compound ($H_2/Cl$) becomes at most 0.7, to a catalyst layer packed with a palladium catalyst supported on active carbon, to subject them to a gas phase reaction to form 2,3,3,3-tetrafluoropropene, and separating the formed 2,3,3,3-tetrafluoropropene from byproduct 1-chloro-2,3,3,3-tetrafluoropropene to isolate the 2,3,3,3-tetrafluoropropene, wherein recycling of 1-chloro-2,3,3,3-tetrafluoropropene is carried out at least once, said recycling comprising blending the byproduct 1-chloro-2,3,3,3-tetrafluoropropene with 1,1-dichloro-2,3,3,3-tetrafluoropropene to form a fresh raw material compound and carrying out its reaction with the hydrogen.

15. The process for producing 2,3,3,3-tetrafluoropropene according to claim 14, wherein the supported amount of palladium in the palladium-supporting active carbon is from 0.1 to 10 mass % based on the active carbon.

16. The process for producing 2,3,3,3-tetrafluoropropene according to claim 14 or 15, wherein hydrogen is introduced in such an amount that the ratio of the number of moles of the hydrogen to the number of moles of chlorine atoms in the raw material compound ($H_2/Cl$) becomes from 0.1 to 0.6, to the catalyst layer.

17. The process for producing 2,3,3,3-tetrafluoropropene according to claim 14, wherein the ratio of the number of moles of hydrogen to the number of moles of chlorine atoms in the raw material compound ($H_2/Cl$) becomes at most 0.6.

18. The process for producing 2,3,3,3-tetrafluoropropene according to claim 1, wherein the raw material compound gas is composed of 1,1-dichloro-2,3,3,3-tetrafluoropropene.

19. The process for producing 2,3,3,3-tetrafluoropropene according to claim 14, wherein the raw material compound gas is composed of 1,1-dichloro-2,3,3,3-tetrafluoropropene.

* * * * *